(12) United States Patent
Klaus et al.

(10) Patent No.: US 7,919,307 B2
(45) Date of Patent: Apr. 5, 2011

(54) SUPPLY SYSTEM FOR CELL CULTURE MODULE

(75) Inventors: Uwe Klaus, Radeberg (DE); Rudolph Luning, Radeberg (DE); Laurence J. Purcell, Weston (CA); Stefan Doring, Dresden (DE)

(73) Assignee: ALPHA PLAN GmbH, Radeberg (DE)

( * ) Notice: Subject to any disclaimer, the term of this patent is extended or adjusted under 35 U.S.C. 154(b) by 1308 days.

(21) Appl. No.: 11/382,150

(22) Filed: May 8, 2006

(65) Prior Publication Data
US 2006/0257998 A1 Nov. 16, 2006

Related U.S. Application Data

(60) Provisional application No. 60/781,915, filed on Mar. 13, 2006.

(30) Foreign Application Priority Data

May 9, 2005 (EP) .................................... 05103824

(51) Int. Cl.
*C12M 3/00* (2006.01)

(52) U.S. Cl. ............... 435/289.1; 435/293.1; 435/288.5; 435/297.4

(58) Field of Classification Search .............. 435/293.1, 435/289.1, 288.5, 297.2, 297.4, 297.5; 422/130
See application file for complete search history.

(56) References Cited

U.S. PATENT DOCUMENTS

| | | | |
|---|---|---|---|
| 5,010,014 A * | 4/1991 | Gebhardt | 435/297.2 |
| 5,126,238 A | 6/1992 | Gebhard et al. | |
| 5,932,178 A * | 8/1999 | Yamazaki et al. | 422/159 |
| 6,001,585 A | 12/1999 | Gramer | |
| 6,432,698 B1 | 8/2002 | Gaugler | |
| 2003/0036192 A1 | 2/2003 | Singh | |
| 2004/0045890 A1 | 3/2004 | Herczeg | |
| 2006/0014274 A1 | 1/2006 | Klaus | |
| 2006/0231139 A1 | 10/2006 | Neumann | |

FOREIGN PATENT DOCUMENTS

| | | |
|---|---|---|
| CA | 2 274 243 | 6/1998 |
| CA | 2 434 842 | 8/2002 |
| CA | 2 498 187 A1 | 3/2004 |

(Continued)

OTHER PUBLICATIONS

Sauer, Ignor M., et al., "The Slide Reactor—A Simple Hollow Fiber Based Bioreactor Suitable for Light Microscopy", Thoughts and Progress, Artificial Organs, 29 (3); pp. 264-267, Blackwell Publishing, Inc., (2005).

Gloeckner, Herma and Lemke, Horst-Dieter, "New Miniaturized Hollow-Fiber Bioreactor for a Vivo Like Cell Culture, Cell Expansion, and Production of Cell-Derived Products", Biotechnol. Prog. 2001, 17, 828-831, 2001 American Chemical Society and American Institute of Chemical Engineers (Aug. 21, 2001).

(Continued)

*Primary Examiner* — William H Beisner
(74) *Attorney, Agent, or Firm* — Scott Raymond Pundsack; Borden Ladner Gervais LLP

(57) ABSTRACT

A device for supplying cell culture modules with nutrients has an arrangement of channels, pumps and valves in or on a plate. The valves may be pinch valves operated by deforming an elastic section of a conduit and the pump may be a pinch valve pump. The channels may be defined, at least in part, by the plate. The pumps, channels and valves may be located within the thickness of the plate. The device may be used to supply nutrients to cell culture modules according to a perfusion operation, a re-circulation operation and/or a combination of both.

6 Claims, 8 Drawing Sheets

FOREIGN PATENT DOCUMENTS

| | | |
|---|---|---|
| CA | 2498187 | 3/2004 |
| CA | 2 525 842 | 12/2004 |
| DE | 10393754 | 3/2004 |
| DE | 10244859 | 4/2004 |
| EP | 0 343 357 | 4/1986 |
| EP | 0 198 032 | 10/1986 |
| EP | 0 371 783 A2 | 6/1990 |
| EP | 1 026 821 A2 | 8/2000 |
| EP | 1 439 384 A2 | 7/2004 |
| JP | 1144969 | 6/1989 |
| JP | 01144969 A2 | 6/1989 |
| JP | 3-172170 | 7/1991 |
| JP | 2003-225 | 1/2003 |
| JP | 2004-147552 | 5/2004 |
| JP | 2005-95165 | 4/2005 |
| JP | 2005-333945 | 12/2005 |
| WO | WO 86/02378 | 4/1986 |
| WO | WO 93/11498 | 6/1993 |
| WO | WO 03/106705 A1 | 12/2003 |
| WO | WO 2004/024303 A2 | 3/2004 |
| WO | 2004033615 | 4/2004 |
| WO | WO 2005/118771 A2 | 12/2005 |
| WO | WO 2005/118771 A3 | 12/2005 |
| WO | WO 2006/037022 A2 | 4/2006 |
| WO | 2006119622 | 11/2006 |

OTHER PUBLICATIONS

Sauer, I. M., et al., "Development of a Hybrid Liver Support System", Medizinische Fakultat der Humboldt Universitat zu Berlin, Berlin, Germany, Annals New York Academy of Sciences, pp. 308-319.

Millis, J. Michael, et al., "Initial Experience with the Modified Extracorporeal Liver-Assist Device for Pateints with Fulminant Hepatic Failure: System Modifications and Clinical Impact", Lippincott Williams & Wilkins, Inc., vol. 74, 1735-1746, No. 12, Dec. 27, 2002.

English Abstract of JP1144969, published Jun. 7, 1989, Nok Corp.

I.M. Sauer et al., "Development of a Hybrid Liver Support System", University of Berlin, pp. 308-318.

J. Michael Millis et al., "Initial Experience with the Modified Extracorporeal Liver-Assist Device for Patients with Fulminant Hepatic Failure: System Modifications and Clinical Impact", Transplantation, vol. 74, pp. 1735-1746, (2002).

I.M. Sauer et al., "The Slide Reactor-A Simple Hollow Fiber Based Bioreactor Suitable for Light Microscopy, Thoughts and Process", Artificial Organs, 29(3), pp. 264-267, Blackwell Publishing, Mar. 2005.

Gloeckner et al., "New Miniaturized Hollow-Fiber Bioreactor for in Vivo Cell Culture, Cell Expansion, and Production of Cell-Derived Products", Biotechnol. Prog. 2001, pp. 828-831.

* cited by examiner

SUPPLY SYSTEM FOR CELL CULTURE MODULE

This is an application claiming the benefit under 35 USC 119(e) of U.S. Provisional Application Ser. No. U.S. 60/781, 915 filed Mar. 13, 2006. This application also claims priority to European Application Serial No. EP 05103824.8 filed May 9, 2005. Application Ser. Nos. U.S. 60/781,915 and EP 05103824.8 are incorporated herein, in their entirety, by this reference to them.

FIELD

This specification relates to devices or processes for cultivating cells.

BACKGROUND

The comments in this background section are not an admission that anything discussed in this section is citable as prior art or part of the common general knowledge of persons skilled in the art in any country.

Some systems for cell cultivation have been developed which provide in some way for the supply of nutrient media to, and the removal of metabolic waste products from, a cell culture. In some systems, cells have been supported on hollow plastic fibers inside of bioreactors. Literature discussing cell cultivation includes the following (1) Sauer, I. M. et al.: The Slide Reactor—a simple hollow fiber based bioreactor suitable for light microscopy; *Artificial Organs* 29 (3): 264-267, 2005; (2) Sauer, I. M. et al.: Development of a hybrid liver support system. *Ann NY Acad Sci* 944: 308-19, (2001); Millis, J. M: et al.: Initial experience with the modified extracorporeal liver-assist device for patients with fulminant hepatic failure: system modifications and clinical impact. *Transplantation* 74: 1735-46; (2002); and, (4) Glöckner, H. et al.: New miniaturized hollow fiber bioreactor for in vivo like cell culture, cell expansion and production of cell-derived products. *Biotechnol Prog* 17: 828-31 (2001).

PCT Publication No. WO 2004/024303 A2, and related U.S. Publication No. 2006/0014274 A1, disclose a fiber cassette having a housing that is delimited by two congruent base surfaces and at least one circumferential surface and has an interior having at least one cavity. At least one layer of fibers is arranged in the interior of the housing essentially parallel to at least one center plane of the housing, wherein ends of the fibers are anchored fixedly in the interior of the housing. A first one of the at least one cavity defines an outer compartment that surrounds the fibers externally. The at least one center plane does not intersect the base surfaces within the outer compartment. The fibers are arranged U-shaped or essentially parallel to one another and end within the interior of the housing. The housing has at least one opening for supplying and/or removing fluids. PCT Publication No. WO 2004/024303 A2 and U.S. Publication No. 2006/0014274 are incorporated herein in their entirety by this reference to them.

SUMMARY

The following summary is intended to introduce the reader to this specification but not to define any invention. Inventions may reside in a combination or sub-combinations of the apparatus elements or process steps described below or in other parts of this document. The invention protected by this document is described in the claims. The inventors do not waive or disclaim their rights to any invention or inventions disclosed in this specification merely by not describing such other invention or inventions in the claims.

The inventors have observed that prior cell cultivation systems involve a complex arrangement of transport hoses, pumps, valves, connectors and other elements for transporting nutrients through a cell culture area. This interferes with economical production of a cell cultivation system, particularly a system of multiple identical culture areas, for example for parallel production to increase output, for drug screening or other applications where it is desirable to grow multiple cultures at the same time. Space requirements of prior systems may also be large.

In an apparatus described herein, a plurality of nutrient or waste transport elements are provided on or inside of, or inside the notional periphery of, a planar transport plate, alternately called a nutrient transport plate. The transport plate is an assembly of elements comprising a solid body and other components collectively adapted to assist in transporting nutrients to, or waste from, a cell culture area or module. The transport plate is planar in the sense that a set of its elements are located within an imaginary plane plus or minus 2 cm. The notional periphery of a transport plate refers to the periphery of a three-dimensional body, for example a parallelepiped, containing the transport plate. A transport plate described in relation to a set of transport elements may still be planar, and have those elements within the notional periphery of the transport plate, despite the presence of other elements attached to the transport plate and extending beyond the notional periphery. Such an apparatus may reduce one or more of the disadvantages of prior nutrient transport systems or at least provide a useful alternative to prior nutrient transport systems or bioreactors.

This specification also describes an apparatus comprising one or more elements formed at least in part by, or attached to, a rigid solid body and arranged for one or more of the supply, removal or recirculation of nutrient media to one or more cell culture modules. The one or more elements for nutrient transport may include one or more of a transport conduit, a valve, a check valve, a connection for a fresh media container or a waste container, a pump, a connection for a cell culture module or an integrated cell culture area. A transport conduit may be formed at least in part by a surface of the solid body. A transport conduit may be a part of a nutrient supply path or a nutrient recirculation path or both. A valve, pump, or connection may be attached to the solid body. A valve may comprise a portion of a transport conduit formed at least in part by a flexible body which may be moved into the portion of the transport conduit to prevent or inhibit flow. A pump may comprise a portion of a transport conduit formed at least in part by a flexible body between two valves or check valves. Deflecting the flexible body into the transport conduit portion causes fluid in the portion of the transport conduit portion to move out of the transport conduit portion through one valve and releasing the flexible body causes fluid to flow into the transport conduit portion through the other valve. Portions of a transport conduit that are part of a valve or pump may include sections of flexible hose. A transport conduit may have a silicone surface.

An apparatus may optionally also include one or more of a sampling connection, a transducer, a sensor mount, a meter, a thermal element or a gassing element. A sensor may be positioned so as to not contact nutrient solution. A connector may be a standard, universal, or frequently used connector to facilitate the integration of an arbitrary cell culture module to the nutrient transport plate. An apparatus may be made of a sterilisable material such as a plastic. This allows an apparatus to be used as a disposable transport system, if the corresponding cell culture module is detachable or also disposable. Metals, glass, ceramics or other materials may also be used. An apparatus may be suitable for, and a process may comprise using an apparatus for, nutrient transport to modules containing or cultivating protozoa, bacteria, yeasts, fungi, plants or cells of vertebrates, for example mammals. An apparatus may be combined with a cell culture module according to WO 2004/024303 A2 or other cell culture modules which may be, for example tubular, planar, rectangular, star-shaped or other shapes.

This specification also describes a process comprising providing an apparatus as described above and using the apparatus, for example by moving the flexible bodies of the apparatus, to transport nutrients through cell culture modules in perfusion, recirculation or a combination of these two operating modes.

BRIEF DESCRIPTION OF THE DRAWINGS

Examples of apparatuses and processes will be described below with reference to the following figures.

DETAILED DESCRIPTION

Various apparatuses or processes will be described below to provide an example of an embodiment of each claimed invention. No embodiment described below limits any claimed invention and any claimed invention may cover processes or apparatuses that are not described below. The claimed inventions are not limited to apparatuses or processes having all of the features of any one apparatus or process described below or to features common to multiple or all of the apparatuses described below. It is possible that an apparatus or process described below is not an embodiment of any claimed invention. The applicants, inventors and owners reserve all rights in any invention disclosed in an apparatus or process described below that is not claimed in this document and do not abandon, disclaim or dedicate to the public any such unclaimed invention by its disclosure in this document.

Figure 1A:
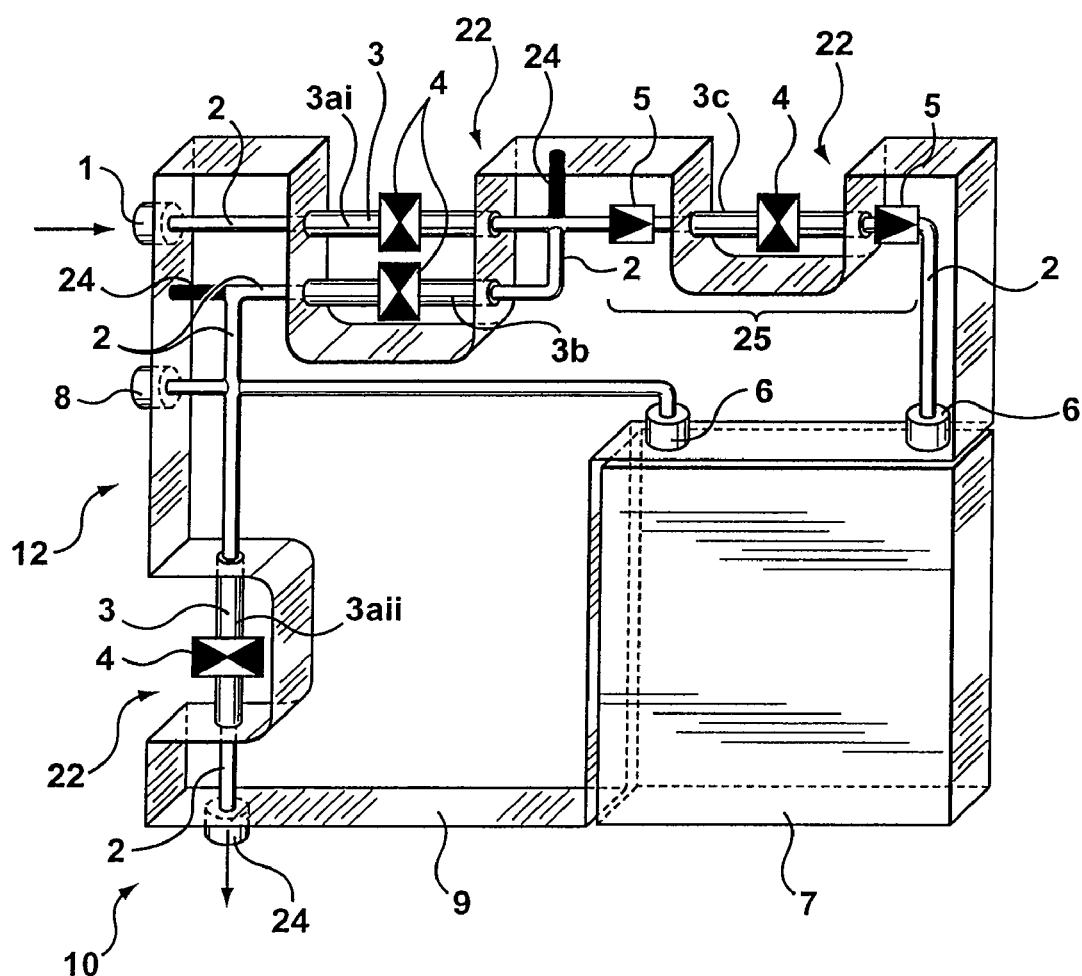
FIG. 1A shows a diagram of a nutrient transport plate and a removable cell culture module.
Figure 1B:
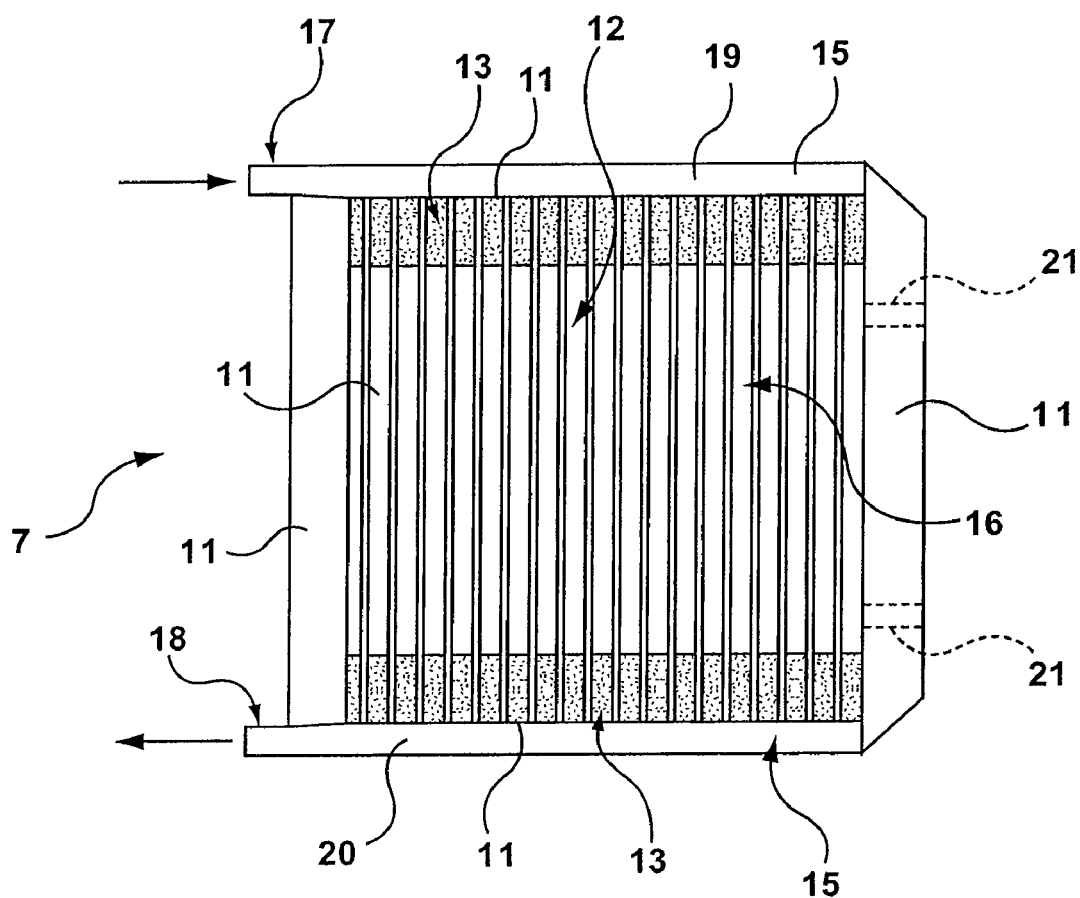
FIG. 1B shows a removable cell culture module adapted to be used with the nutrient transport plate of FIG. 1A.

Referring to FIG. 1A, a bioreactor 10 comprises a nutrient transport plate 12 and a cell culture module 7. Cell culture module 7 is plugged into, and optionally may be removed from, cell culture module connections 6. Cell culture module connections 6 may be holes machined in solid body 9 optionally with fittings (not shown) inserted into them. An example of a cell culture module 7 is shown in more detail in FIG. 1B. As shown, the cell culture module 7 has a cover removed from it that would otherwise enclose an outer compartment 16 and parts of an inner compartment 15. Inner compartment 15 also includes the lumens of hollow fiber membranes 12. The walls of hollow fiber membranes 12 and potting compound 13 as well as a base structure 11 and the cover (not shown), separate inner compartment 15 from outer compartment 16. Cells may grow on the membranes 12 or otherwise in second compartment 16. Nutrients may be supplied to the cells through the first compartment 15 and the walls of membranes 12. In particular, a nutrient solution can be input into supply port 17, into a first channel 19 portion of first compartment 15, through the lumens of membranes 12, into a second channel 20 portion of first compartment 15 and out through a waste port 18. While traveling through this path, some nutrients, for example carbohydrates or gases, pass through the walls of membranes 12 to be consumed by cells in second compartment 16. Some waste products released by the cells travel from second compartment 16 through the walls of membranes 12 and are carried away with the nutrient solution. Cell culture module 7 is attached to nutrient transport plate 12 by inserting supply port 17 and waste port 18 into cell culture module connections 6. Ports 17 and 18 may be glued into connections 6 for a permanent attachment, or removably sealed together through a press in or other fit. Optionally, cell culture module 7 may have auxiliary ports 21 to allow for adding or removing substances to second compartment 16 without passing through the walls of membranes 12. The auxiliary ports 21 can be used, for example, to extract cells or cell products, secretions, viruses, proteins or low molecular weight substances. The bioreactor 10 can thus be used for a variety of applications including, for example, growing high density cell cultures, testing or screening for the reaction of cell cultures to various substances, or harvesting products made by cells.

Solid body 9 of nutrient transport plate 12 may be made from a sheet of a rigid material, for example a hard plastic, with a thickness in the range of, for example, 3 mm to 10 mm. Solid body 9 may be made by cutting the sheet of material to a selected width and length, for example in the range of 3 cm to 15 cm. Openings 22 may be drilled, cut, milled or otherwise made in the sheet material. Transport channels 2 may be made by drilling into the edges of solid body 9. Plugs 24 may be inserted into transport channels 2 as required to close parts of holes made by the drilling operations but not required for the transport channels 2. Breaks in flow paths across openings 22 are spanned by transport tubes 3, for example flexible tubes slipped over fittings, not shown, inserted into the transport channels 2 where they meet the boundaries of openings 22. Transport channels 2 and transport tubes 3 together form conduits or passageways making up the flow paths described below. The transport tubes 3 may be made of silicone where oxygen transfer to the cells is desired, or of other materials when oxygen transfer is not desired or is provided in the nutrient feed or otherwise. A nutrient supply is connected to the nutrient transport plate 12 through nutrient connector 1 which may comprise a fitting slipped into a transport channel 2 or a larger hole in rigid body 9. Waste solution may leave transport plate 12 through a waste connector 24 which may be made as described for nutrient connector 1. Samples may be extracted from a sample valve 8 which may comprise, for example, a true valve, an opening with a removable cap, or a self sealing septum.

The nutrient transport plate 12 provides two basic flow paths. A first flow path starts at the nutrient connector 1 and ends at waste connector 24 after passing through an area containing waste nutrient, for example the first compartment 15 of cell culture module 7 or an integrated cell culture area or a part of the second flow path described below. A second flow path travels in a loop through the nutrient transport plate 12 from a first cell culture module connection 6 to the other and then through the first compartment 15 of cell culture module 7 back to the first cell culture module connection 6, or through a similar path involving an integrated cell culture area. While nutrient is flowing through the second flow path, a connection to nutrient connector 1 may be left open so that nutrient can be drawn in to replace nutrient consumed by the cells. Between the two flow paths, fresh nutrient solution can flow from a nutrient source to membranes 12, old nutrient solution can flow out to a waste container or drain, or a nutrient solution can re-circulate though the membranes 12. Further, a bioreactor 10 can be operated cyclically with, for example a period of flow through the first flow path, then a period of flow through the second flow path repeated in cycles. Control and propulsion through these flow paths may be provided as described below.

A portion of some or all of transport tubes 3 may be part of a pinch valve body 4. The pinch valve body 4 works with a pinching device (see element 44 of FIG. 3) of a pinching unit (see element 46 of FIG. 3). The pinching device is operable to pinch a transport tube 3 so as to fully or partially close its inner bore and prevent or inhibit nutrient flow and thereby provide a valve. The pinching device may have an actuator, for example a solenoid or a pneumatic or hydraulic piston, movable toward a solid fixed or movable surface on the other side of a transport tube 3. Two or more nutrient transport plates 12 may be stacked over each other and the operative parts of the pinching device may extend through the openings 22 of the stack such that a pinching machine may simultaneously pinch the transport tubes 3 of the two or more nutrient transport plates. For example, when transport tube 3aii is closed and transport tube 3b (and optionally transport tube 3aii) is open, the second flow path is provided. When transport tube 3b is closed and transport tubes 3a are open, the first flow path is provided. Flow through the first flow path can also be provided by having transport tubes 3ai and 3b closed and transport tube 3aii open while transport tube 3c is pinched as part of the operation of pump 25 described below, closing transport tube 3aii and opening transport tubes 3ai and 3b while transport tube 3c remains pinched, then releasing transport tube 3c. According to that operation, transport tubes 3ai and 3b are operated simultaneously and may be activated by one pinching device 44 to be described further below.

Nutrient transport plate 12 has a pump 25 comprising a pair of check valves 5 inserted in or connected to transport channels 2 opening into the opposed sides of an opening 22. The check valves 5 are connected together by a transport tube 3c spanning the opening 22 and providing part of a pinch valve body 4. However, because of the check valves 5, pinching the transport tube 3c reduces the volume inside the transport tube and forces nutrient fluid towards one of the cell culture module connectors 6. When transport tube 3c is released, or unpinched, it moves back towards its full volume by means of its elastomeric walls returning to their unstressed state. This draws nutrient from the other of the cell culture module connections 6 or the nutrient connector 1 depending on which of transport tubes 3a or 3b is open. If transport tubes 3a are open and transport tube 3b is closed, pinching transport tube 3c causes nutrient solution to flow through the first flow path. If transport tubes 3a are closed and transport tube 3b is open, pinching transport tube 3a causes nutrient solution to circulate through the second flow path. When moving fluid through this flow path, transport tube 3b, or parts of other transport tubes, may swell temporarily to take up a volume of nutrient solution displaced by pinching transport tube 3c. The bioreactor 10 may also be operated by alternating between the flow paths. For example, transport tube 3c may be pinched one or more times while the first flow path is open to expel old nutrient fluid containing waste products and intake fresh nutrient solution. Thereafter, transport tube 3c may be pinched one or more times to recirculate nutrient fluid. Then these two steps above are repeated so as to cycle back and forth between refreshing and recirculating the nutrient solution. For example, a cycle may comprise repetitions of pinching transport tube 3c once to refresh nutrient, followed by pinching transport tube 3c for 2 to 10 times to recirculate the nutrient solution. Alternately, an additional check valve may be inserted into nutrient connector 1 to allow nutrient solution to enter into but not exit from nutrient connector 1. Then transport tubes 3ai and 3b may be left open while transport tube 3aii is pinched but still left slightly open. In this configuration, pinching transport tube 3c causes a continuous recirculation but with a continuous bleed of waste and feed of fresh nutrient solutions. Check valves 5 may be optionally be replaced by other valves, for example pinch valves, operated so as to mimic the action of pinch valves 4.

Figure 2:
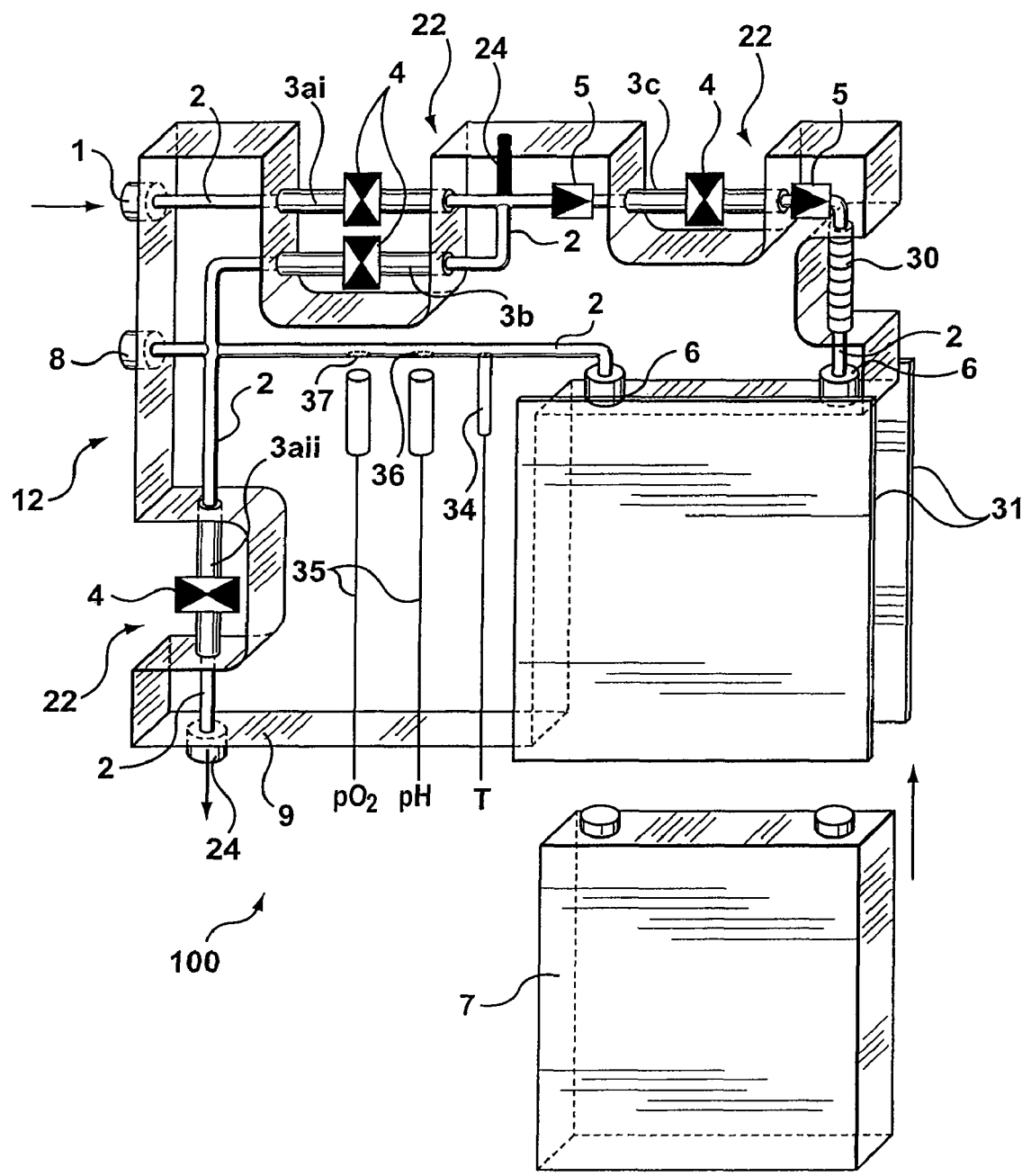
FIG. 2 shows a nutrient transport plate having examples of additional process monitoring or control elements.

FIG. 2 shows a second bioreactor 100. Second bioreactor 100 includes the components of bioreactor 10 of FIG. 1A. However, second bioreactor 100 also has various optional additional components for process implementation, monitoring or control. Gassing element 3 is a section of tubing made of a highly oxygen permeable material, for example silicone. Temperature elements 31 may heat or cool the cell culture module 7. Temperature sensor 34 is inserted into a hole drilled into the edge of solid body 9 intersecting a transport channel 2. Temperature sensor 34 measures nutrient solution temperature and may be connected to temperature elements 31 in a control or feedback loop. One or more optical sensors 5 may be inserted into holes drilled into the edge of solid body 9 so as to be near, but not fluidly connected to a transport channel 2. Optical sensors 35 may comprise a pH sensitive transducer 36 or a dissolved oxygen level sensitive transducer.

Figure 3:
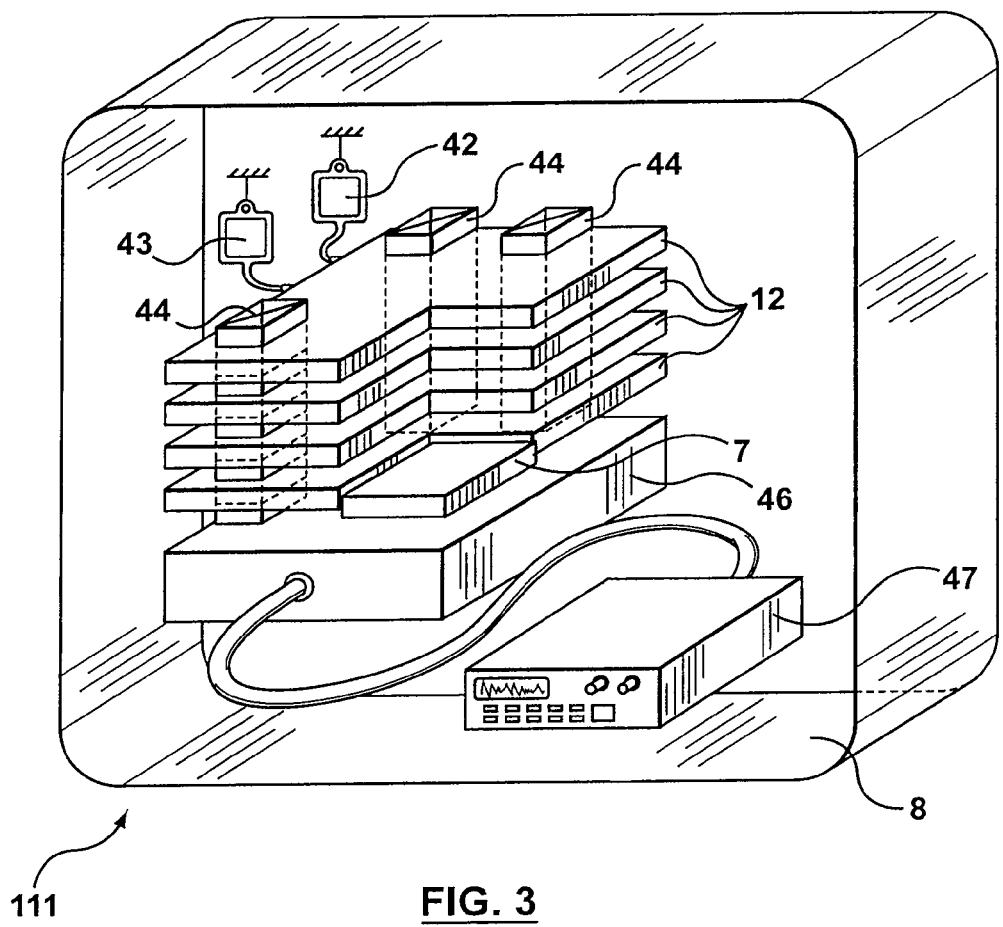
FIG. 3 shows a system comprising several vertically stacked nutrient transport plates, a nutrient solution container, a waste container, a pumping/valving unit and a control unit in a temperature controlled cabinet.

FIG. 3 shows an assembled cell cultivation system 111 having one or more stacked nutrient transport plates 12. Nutrient transport plates 12 are connected in parallel to a nutrient container 2 and a waste container 43. Pinching devices 44 are situated over the nutrient transport plates so as to be able to pinch the transport tubes 3 of the nutrient transport plates 12 to provide valve operations and pumping as described in relation to FIG. 1. Pinching devices 44 are part of or attached to a pinching unit 46 which powers or drives the pinching devices 44. Pinching unit 46 is controlled by a control unit 47. Control unit 47 may also be connected to the various sensors, meters or transducers of FIG. 2, additional sensors or controllers connected to the nutrient transport plates 12 or system control or monitoring elements, such as flow or volume meters connected to or in line with containers 42, 43. Control unit 47 may be a programmable logic controller (PLC) for example a "C"-control-unit. The system 111 is optionally located within a controlled environment chamber 8.

In an example of the use of a bioreactor, a cell culture module according to International Publication No. WO 2004/024303 A2, had a 0.5 ml cell culture space fed nutrients through hollow fiber membranes and connections for the inoculation of cells in the cell culture space. The module was integrated in a planar plastic nutrient transport plate. Nutrient and waste supply and removal for the cell culture module was provided by way of integrating the module into the transport plate. Sampling was enabled through a septum integrated in the transport plate. The entire system was sterilized with gamma radiation.

Figure 4:
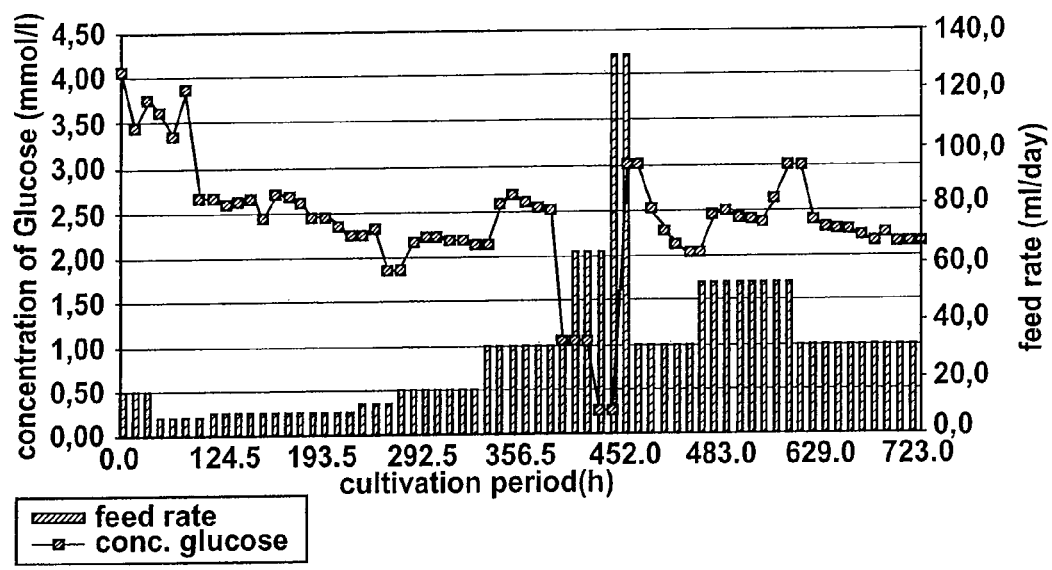
FIG. 4 shows the glucose concentration in the nutrient solution as well as the feed rate of the nutrient solution throughout the duration of a culture.

The cell culture space was inoculated with a Chinese Hamster Ovary cell line. Cells were cultivated by means of the nutrient solution transport plate, in that a container with commercially available cell culture nutrient medium, to which 0.02% Human Serum Albumin was added, was connected to the inlet of the nutrient solution transport plate, and in that a waste collection container for waste nutrient solution was connected to the outlet of the transport plate. The cultivation was conducted following inoculation of the cell culture chamber of the culture module with a total cell count of 4.51 E6 cells at a vitality rate of 75.6%. The bioreactor, including a pumping/valving unit, was placed in a controlled environment chamber, specifically a $CO_2$-incubator at a temperature of 37° C. and 5% $CO_2$. Every work day samples of recycling nutrient solution were taken through the septum integrated into the transport plate. The associated glucose value was determined, and the feed rate was adjusted according to the glucose consumption in order to ensure appropriate supply of glucose to the cells inside the culture module. The cultivation was conducted over a period of 30 days. Subsequently, the cells were fixed with glutardialdehyde and embedded in synthetic resin. At that time, the increase in cell mass could be detected macroscopically and from the glucose consumption. The glucose concentration inside the feed nutrient solution, at the outlet of the cell culture module, as well as the feed rate over the course of the 30 day culture period are shown in FIG. 4.

Figure 5:
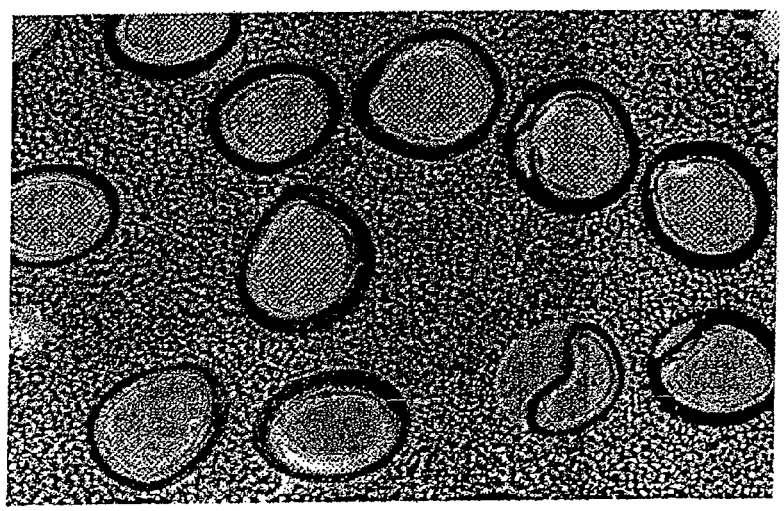
FIG. 5 is a photograph of cells in a 10 μm thick slice of a cell culture module after fixation of the cells showing hollow fiber membranes (large circles showing fiber walls and lumens) and a tissue of the cells colored with a hematoxylin-eosine and 40 times enlarged.

Throughout the entire period, the cultivated cells continuously consumed glucose. The condition of the cells inside the cell culture module can be influenced by means of process control, for example rate of feed and concentration of glucose. An accumulation of cells was clearly visible after the first third of the cultivation. Organ like structures could be detected through the clear plastic cover of the cell culture module. The arrangement of the cells inside the culture module interspersed with hollow fiber membranes is shown in FIG. 5. The glucose consumption and the dense arrangement of the cells in the profiles demonstrate that the planar nutrient transport plate can conduct necessary functions of a bioreactor transport system. Specifically, the transport plate can supply nutrients, including for example oxygen or carbon dioxide, to a cell culture module and discharge wastes from the cell culture module. The preferred but optional arrangement of a sensor or a sampling port downstream of the cell culture module enables the accurate detection of current nutrient solution parameters and therefore the condition of the cells.

Figure 6:
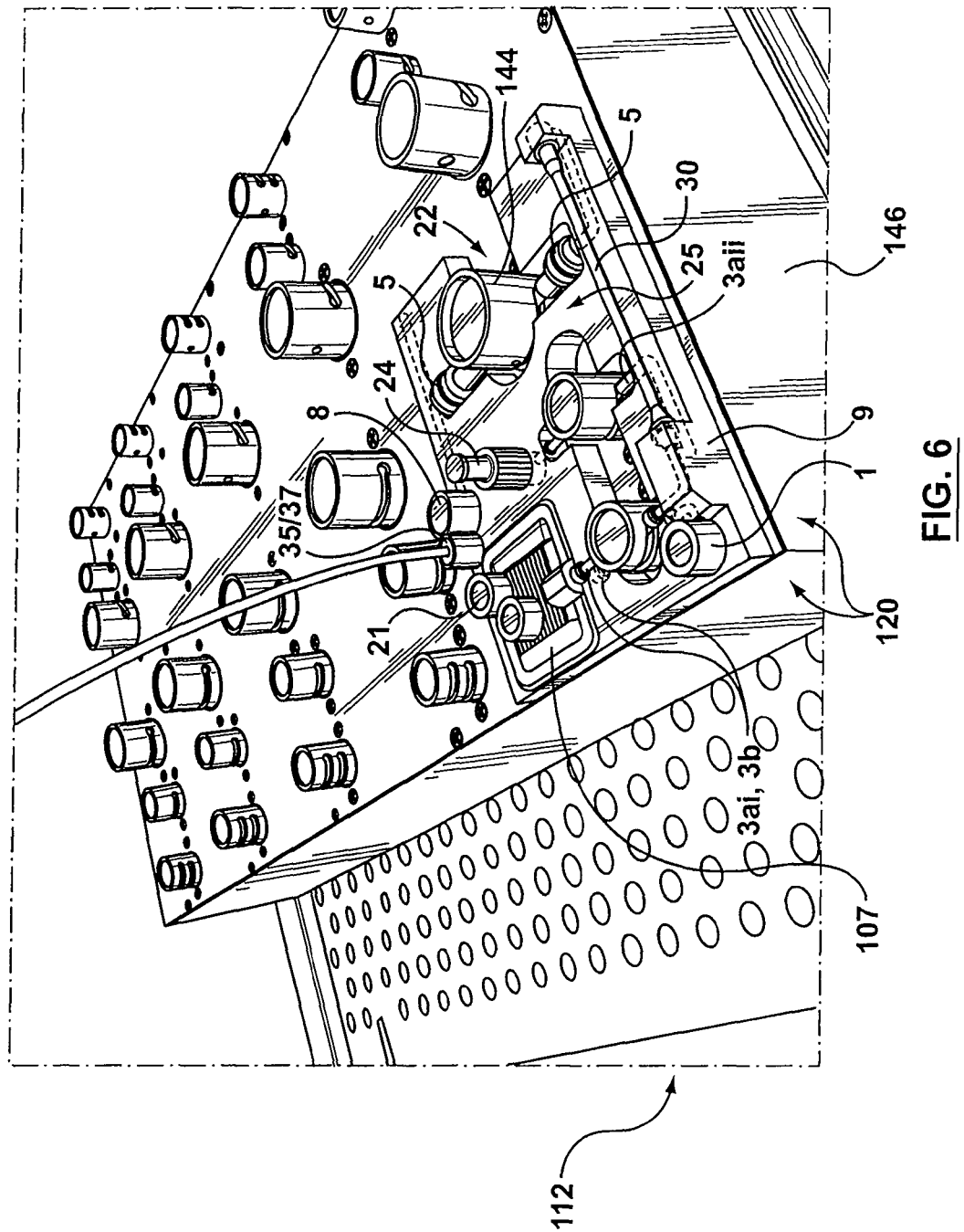
FIG. 6 is a photograph of another transport plate on another pumping/valving unit.
Figure 7:
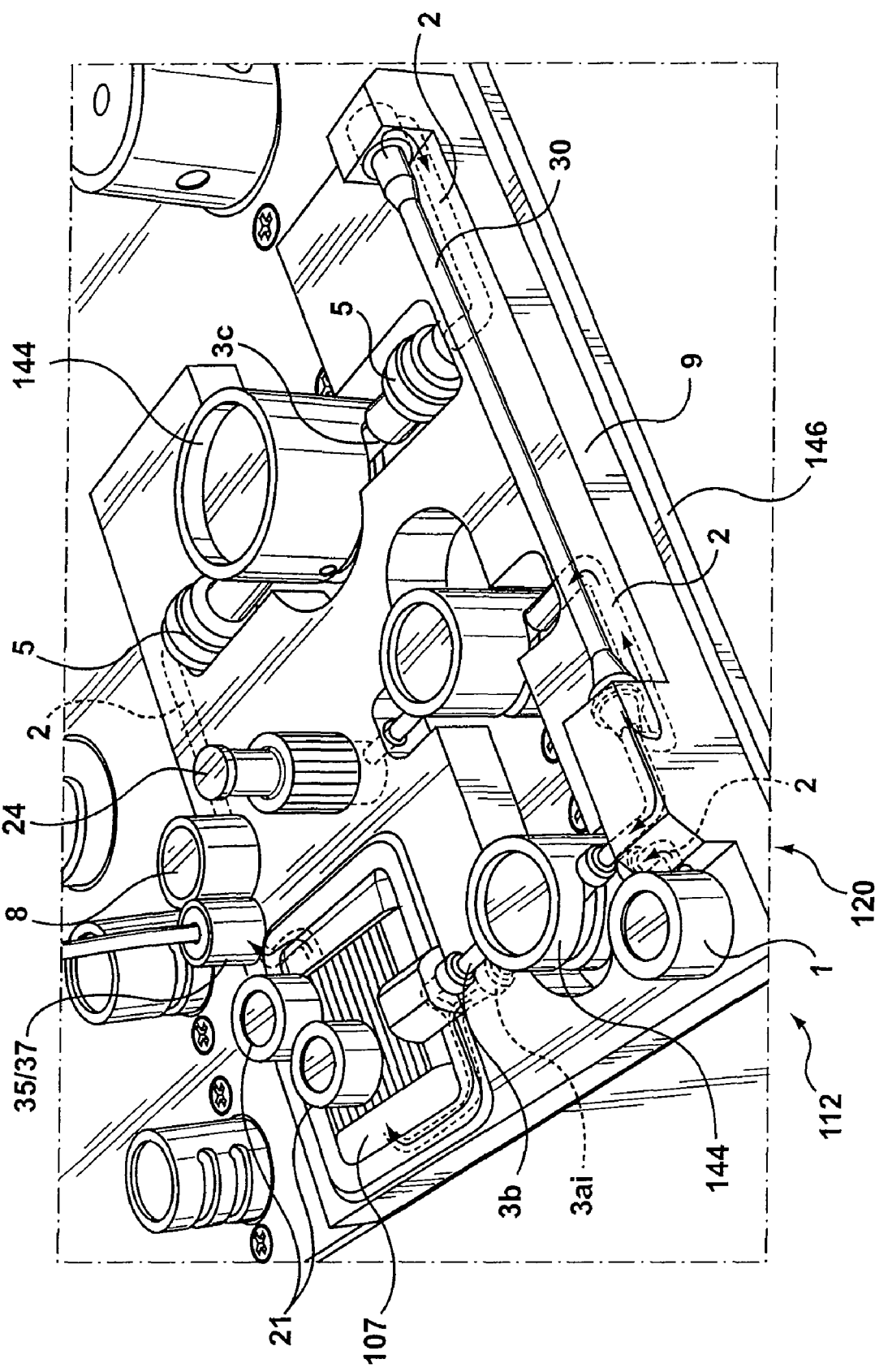
FIG. 7 is an enlarged view of a portion of the photograph of FIG. 6.
Figure 8:
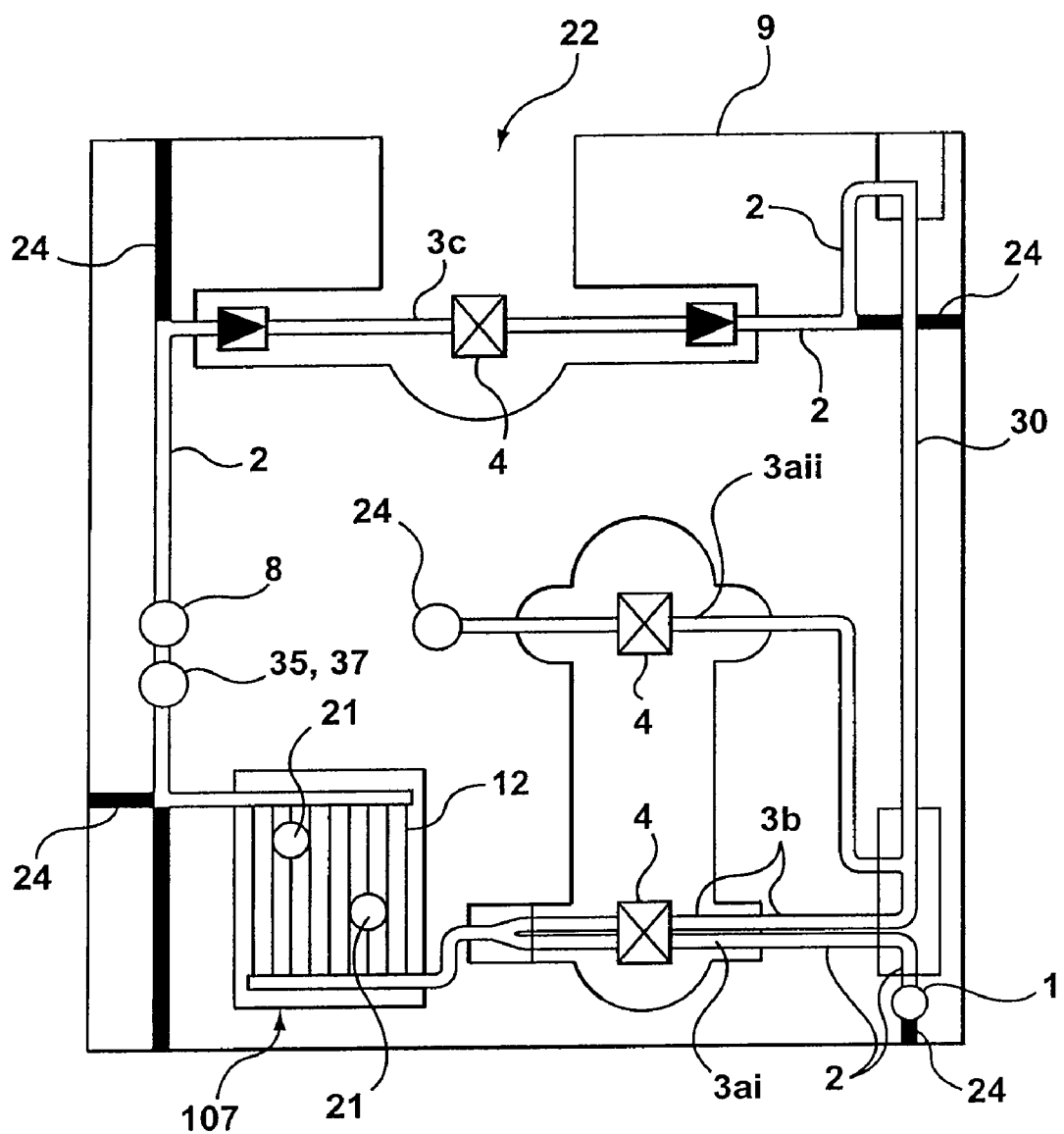
FIG. 8 is a schematic diagram corresponding to a bioreactor shown in FIGS. 7 and 8.

FIGS. 6 and 7 show a second system 112 having a third bioreactor 120, a second pinching device 146. A controller is also part of the second system 112 but not shown. Second system 112 has the capacity to operate 10 third bioreactors 120 at the same time, although similar systems may be made to operate other numbers, for example between 1 and 100, of bioreactors. In second system 112, the third bioreactors 120 are laid out in a grid spread horizontally across an upper surface of second pinching device 146. For each third bioreactor 120, second pinching device 146 has three second pinchers 144 each comprising a cylindrical body slotted horizontally to admit a transport tube 3 and containing a solenoid operable to pinch a transport tube 3 in the slot. Openings 22 in third bioreactors 120 are sized and shaped to allow a third bioreactor 120 to be lowered vertically over the second pinchers 44 and then slid horizontally to locate transport tubes 3, which are parallel to each other, within the horizontal slots. The third bioreactors 120 can be removed by reversing these movements. A selected third bioreactor 120 can be removed while cultivation continues with the other third bioreactors 120, optionally without even pausing the motion of the second pinchers 44, since a short horizontal movement of a third bioreactor 120 moves the transport tubes 3 out of the slots of the second pinchers 44. Third bioreactor 120 differs from the previously described bioreactors 10, 100 in some ways. For example, various components are placed on top of, or sticking up from the top of, solid body 9 since the third bioreactors 120 will be arrayed horizontally rather than vertically. In particular, transport tube 3b is above transport tube 3ai rather than beside it. For further example, third bioreactor 120 also has an integrated cell culture area 107 rather than a distinct cell culture module 7. For yet further example, waste connector 24 is located upstream, rather than downstream, of cell culture area 107. In other respects, third bioreactor 120 is like bioreactors 10, 100 and similar components are given the same reference numeral and the description given above for those components applies to third bioreactor 120 but for any modifications apparent from FIG. 6 or 7 or the description of them. FIG. 8 provides a schematic diagram corresponding to the third bioreactor 120.

The second system 112 could be modified to have channels for the supplying the third bioreactors 120 integrated into the pinching device 146. Automatic sampling or surveillance, for example using optical systems, may also be possible. A clear upper part of the cell culture area 107 allows visual monitoring of the cell culture space and could also allow for machine vision monitoring to be used.

The invention or inventions which are currently claimed in this document are described in the following claims.

We claim:

1. An apparatus comprising,
    a) a rigid solid body;
    b) one or more flexible bodies connected to the rigid solid body;
    c) first and second check valves within or connected to the rigid solid body;
    d) waste and nutrient connectors;
    e) a cell culture area within or connected to the rigid solid body, the cell culture area having an inlet and an outlet; wherein;
    f) the rigid solid body, the one or more flexible bodies and the check valves define i) a first flow path between the nutrient connector and the inlet of the cell culture area and between the outlet of the cell culture area and the waste connector and ii) a second flow path between the outlet of the cell culture area and the inlet of the cell culture area, wherein the second flow path passes through the check valves and a portion of the second flow path between the check valves is deformable to reduce the interior volume of the portion of the second flow path between the two check valves, the check valves and the portion of the second flow path between them thereby adapted to act as a pump.

2. The apparatus of claim 1 wherein at least one flexible body may be deformed to selectively open or close a flow path.

3. An apparatus according to claim 1 having both flow paths configured such that deforming one or more of the flexible bodies may open one flow path while closing the other.

4. A system comprising an apparatus according to claim 1 and one or more of an actuator, a controller, a nutrient supply or a waste container.

5. The apparatus of claim 1 wherein the cell culture area comprises a plurality of hollow fiber membranes each having a) a first end in communication with the inlet of the cell culture area and b) a second end in communication with the outlet of the cell culture area.

6. An apparatus according to claim 1 wherein the first flow path also passes through the check valves and the portion of the second flow path between the check valves.

* * * * *